US009745544B2

(12) United States Patent
Miracle et al.

(10) Patent No.: US 9,745,544 B2
(45) Date of Patent: Aug. 29, 2017

(54) WHITENING AGENTS FOR CELLULOSIC SUBSTRATES

(71) Applicant: The Procter & Gamble Company, Cincinnati, OH (US)

(72) Inventors: Gregory Scot Miracle, Liberty Township, OH (US); Sanjeev Kumar Dey, Spartanburg, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 59 days.

(21) Appl. No.: 14/881,224

(22) Filed: Oct. 13, 2015

(65) Prior Publication Data

US 2017/0101603 A1 Apr. 13, 2017

(51) Int. Cl.
*C07D 333/36* (2006.01)
*C11D 3/42* (2006.01)
*C11D 3/00* (2006.01)
*C11D 3/386* (2006.01)
*C11D 3/50* (2006.01)
*C11D 3/40* (2006.01)

(52) U.S. Cl.
CPC ................ *C11D 3/42* (2013.01); *C11D 3/001* (2013.01); *C11D 3/0021* (2013.01); *C11D 3/38627* (2013.01); *C11D 3/40* (2013.01); *C11D 3/505* (2013.01)

(58) Field of Classification Search
CPC ..... C07D 333/36; C11D 3/42; C11D 11/0017; C11D 17/042; C11D 3/3917; C11D 3/392
See application file for complete search history.

(56) References Cited

U.S. PATENT DOCUMENTS

| | | | |
|---|---|---|---|
| 4,137,243 A | 1/1979 | Farmer | |
| 4,313,731 A | 2/1982 | Imahori et al. | |
| 4,666,519 A | 5/1987 | Akiyama et al. | |
| 5,039,782 A | 8/1991 | Langer et al. | |
| 5,591,833 A | 1/1997 | Hines et al. | |
| 8,183,197 B2 | 5/2012 | Prabhat et al. | |
| 9,187,717 B2 | 11/2015 | Torres et al. | |
| 2005/0288206 A1 | 12/2005 | Sadlowski et al. | |
| 2008/0119643 A1 | 5/2008 | Lennartz et al. | |
| 2008/0177089 A1 | 7/2008 | Sadlowski et al. | |
| 2008/0177090 A1 | 7/2008 | Valenti et al. | |
| 2009/0312220 A1* | 12/2009 | Boutoille | C11D 3/40 510/277 |
| 2014/0082851 A1* | 3/2014 | Sivik | D06L 4/629 8/137 |
| 2015/0074919 A1 | 3/2015 | Miracle | |
| 2015/0111808 A1* | 4/2015 | Miracle | C11D 3/42 510/325 |

FOREIGN PATENT DOCUMENTS

| | | | |
|---|---|---|---|
| DE | 3035912 | A1 | 4/1981 |
| EP | 2166077 | * | 3/2010 |
| GB | 1 324 303 | A | 7/1973 |
| JP | 47026417 | B | 10/1972 |
| JP | 03159786 | A | 7/1991 |
| WO | WO 2006/042801 | A1 | 4/2006 |
| WO | WO 2006/045375 | A1 | 5/2006 |
| WO | WO 2007/084729 | A2 | 7/2007 |
| WO | WO 2008/087497 | A1 | 7/2008 |
| WO | WO 2008/091524 | A1 | 7/2008 |
| WO | WO 2009/030344 | A2 | 3/2009 |
| WO | 2011082840 | * | 7/2011 |
| WO | WO 2011/082840 | A1 | 7/2011 |
| WO | WO 2011/098356 | A1 | 8/2011 |
| WO | 2013142486 | * | 9/2013 |
| WO | WO 2013/189615 | A1 | 12/2013 |
| WO | WO 2013/189640 | A1 | 12/2013 |
| WO | WO 2014/177369 | A1 | 11/2014 |
| WO | WO 2015/139903 | A1 | 9/2015 |

OTHER PUBLICATIONS

U.S. Appl. No. 14/881,218, filed Oct. 13, 2015, Miracle, et al.
U.S. Appl. No. 14/881,231, filed Oct. 13, 2015, Miracle, et al.
SciFinder®, 2015 10 26 o m-aminoalkoxyphenol azo dyes, Copyright © 2015, American Chemical Society (ACS), 27 pages.
SciFinder®, 2015 10 22 Polyglycerol azo dye references, Copyright © 2015, American Chemical Society (ACS), 14 pages.
SciFinder®, 2015 03 06 Glycidol aniline azo dyes detergent ref, Copyright © 2015, American Chemical Society (ACS), 24 pages.
International Search Report; International Application No. PCT/US2016/054265; date of mailing Dec. 13, 2016; 13 pages.
International Search Report; International Application No. PCT/US2016/054266; date of mailing Dec. 12, 2016; 13 pages.
International Search Report; International Application No. PCT/US2016/054267; date of mailing Dec. 14, 2016; 13 pages.

* cited by examiner

*Primary Examiner* — Charles Boyer
(74) *Attorney, Agent, or Firm* — John T. Dipre; Steven W. Miller

(57) ABSTRACT

The present application relates to novel whitening agents for cellulosic substrates. The whitening agents are comprised of at least two constituents: at least one chromophore constituent and at least one polymeric constituent. Suitable chromophore components generally fluoresce blue, red, violet, or purple color when exposed to light, or they may absorb light to reflect these same shades. This disclosure also relates to laundry care compositions including but not limited to liquid and/or powder laundry detergent formulations and rinse added fabric softening (RAFS) compositions that comprise such whitening agents.

11 Claims, No Drawings

WHITENING AGENTS FOR CELLULOSIC SUBSTRATES

TECHNICAL FIELD

The present application relates to novel whitening agents for cellulosic substrates. The whitening agents are comprised of at least two constituents: at least one chromophore constituent and at least one polymeric constituent. Suitable chromophore components generally fluoresce blue, red, violet, or purple color when exposed to light, or they may absorb light to reflect these same shades. These whitening agents may be ideal for use in laundry care compositions including but not limited to liquid and/or powder laundry detergent formulations and rinse added fabric softening (RAFS) compositions.

BACKGROUND

The use of whitening agents, either optical brighteners or blueing agents, in textile applications is well known in the prior art. As textile substrates age, their color tends to fade or yellow due to exposure to light, air, soil, and natural degradation of the fibers that comprise the substrates. Thus, the purpose of whitening agents is generally to visually brighten these textile substrates and counteract the fading and yellowing of the substrates. Typically, whitening agents may be found in laundry detergents, fabric softeners, or rinse aids and are therefore applied to textile substrates during the laundering process. However, it is important that whitening agents function to brighten treated textile substrates without causing undesirable staining of the textile substrates.

Cellulosic substrates, in particular, tend to exhibit a yellow hue after exposure to light, air, and/or soiling. This yellowness is often difficult to reverse by normal laundering procedures. As a result, there exists a need for improved whitening agents which are capable of eliminating the yellowness exhibited by ageing cellulosic substrates. By utilizing such improved whitening agents, the life of the textile substrates, such as clothing articles, bed and table linens, towels, etc., may be extended.

The present whitening agent offers advantages over the prior art and emit light with wavelengths in the range of blue, red, violet, purple, or combinations thereof upon exposure to ultraviolet light (or, they absorb light to produce the same shades) in order to neutralize the yellowness of cellulosic substrates. The present compounds function ideally as whitening agents for substrates comprised of cellulose, polyester, nylon and mixtures thereof and may be incorporated into laundry detergent formulations for use by consumers during the laundering process.

SUMMARY OF INVENTION

The present disclosure relates to laundry care compositions comprising a laundry care ingredient and a whitening agent. The whitening agent is an nonionic amphiphilic oxygen-linked nonionic dye selected from the group consisting of acridines, anthraquinones, azines, azos, benzodifuranes, benzodifuranones, carotenoids, coumarins, cyanines, diazahemicyanines, diphenylmethanes, formazans, hemicyanines, indigoids, methanes, naphthalimides, naphthoquinones, nitros, nitrosos, oxazines, phthalocyanines, pyrazoles, stilbenes, styryls, triarylmethanes, triphenylmethanes, xanthenes and mixtures thereof.

The present disclosure also relates to laundry care compositions including but not limited to liquid and/or powder laundry detergent formulations and rinse added fabric softening (RAFS) compositions that comprise such whitening agents.

DETAILED DESCRIPTION

As used herein, "cellulosic substrates" are intended to include any substrate which comprises at least a majority by weight of cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Articles formed from cellulosic fibers include textile articles such as fabrics. Articles formed from pulp include paper.

As used herein, the term "laundry care composition" includes, unless otherwise indicated, granular, powder, liquid, gel, paste, bar form and/or flake type washing agents and/or fabric treatment compositions.

As used herein, the term "fabric treatment composition" includes, unless otherwise indicated, fabric softening compositions, fabric enhancing compositions, fabric freshening compositions and combinations there of. Such compositions may be, but need not be rinse added compositions.

As used herein, the articles including "the", "a" and "an" when used in a claim, are understood to mean one or more of what is claimed or described.

As used herein, the terms "include", "includes" and "including" are meant to be non-limiting.

As used herein, the term "non-ionic" refers to any of many organic compounds devoid of cationic or anionic substituents and thus lacking any ionic charge at a neutral pH.

As used herein, the term "amphiphilic" refers to any of many organic compounds composed of hydrophilic and hydrophobic portions. A compound is determined to be amphiphilic for the purposes of the present invention when the compound partitions between deionized water and dodecane at 25° C. such that the compound is predominantly in the water layer. Amphiphilic compounds are determined to be amphiphilic whitening agents if the amphiphilic compound qualifies as a shading dye according to the test methods disclosed herein.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

The whitening agents of the present invention may be dyes, pigments, or polymeric colorants comprising a chromophore constituent and a polymeric constituent covalently bound to one another. It will be understood by those skilled in the art that the whitening agents are not two separate molecules, one comprising a chromophore and the other comprising a polymer, but rather one molecule and that the chromophore constituent and the polymeric constituent are distinct parts of the same molecule. Moreover, the polymeric constituent is bound directly to a oxygen atom on the chromophore constituent. It will further be understood that inclusion of the polymeric constituent, as with all polymeric compounds, may produce a mixture of molecules which incorporate different quantities of monomeric units. For example, during a typical ethoxylation process the randomness of the ethylene oxide addition results in a mixture of oligomers with different degrees of ethoxylation. As a consequence of its ethylene oxide number distribution, which often follows a Poisson law, a commercial material contains substances with somewhat different properties. For example, in one aspect the product resulting from an ethoxylation is not a single compound containing five ($CH_2CH_2O$) units as a general structure may suggest. Instead, the product is a mixture of several homologs whose total of ethylene oxide units may vary from about 2 to about 10. Industrially relevant processes will typically result in such mixtures, which may normally be used directly to provide the fabric shading dye, or less commonly may undergo a purification step.

The whitening agent chromophore constituent may be selected from acridines, anthraquinones, azines, azos, benzodifuranes, benzodifuranones, carotenoids, coumarins, cyanines, diazahemicyanines, diphenylmethanes, formazans, hemicyanines, indigoids, methanes, naphthalimides, naphthoquinones, nitros, nitrosos, oxazines, phthalocyanines, pyrazoles, stilbenes, styryls, triarylmethanes, triphenylmethanes, xanthenes and mixtures thereof. Preferably, the whitening agent is ananthraquinone or an azo dye, and even more preferably the whitening agent is an azo dye. The chromophore constituent is characterized in that it emits or absorbs wavelength to provide a color on substrates in the range of blue, red, violet, purple, or combinations thereof upon exposure to light. Preferably, the chromophore constituent exhibits an absorbance spectrum value from about 520 nanometers to about 640 nanometers in water, and more preferably from about 570 nanometers to about 610 nanometers in water. Preferably, the chromophore constituent exhibits an emission spectrum value from about 400 nanometers to about 480 nanometers in water.

The whitening agent of the present invention may be characterized by the following structure:

Formula I

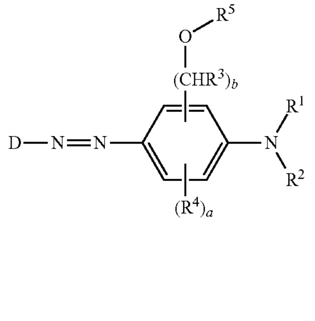

wherein each $R^4$ is independently selected from the group consisting of alkyl, oxyalkyl, oxyaryl, sulfonamidoalkyl, sulfonamidoaryl, amidoalkyl, amidodialkyl, amidoaryl, amidodiaryl, halogen, thioalkyl and thioaryl;

wherein the index a is an integer from about 0 to about 3; the index b is an integer from about 0 to about 1;

wherein D is an aromatic or heteroaromatic group;

wherein $R^1$ and $R^2$ are independently selected from the group consisting of H and unsubstituted or substituted $C_1$ to $C_{12}$ alkyl chains, optionally the alkyl chains comprise ether (C—O—C), ester and/or amide links, optionally the alkyl chains are substituted with —Cl, —Br, —CN, —$NO_2$, —$SO_2CH_3$, —OH and mixtures thereof;

wherein $R^3$ is selected from H and $C_1$-$C_6$ alkyl;

wherein $R^5$ is selected from the group consisting of:

(a) $[(CH_2CR'HO)_x(CH_2CR''HO)_yH]$ wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x ($CH_2CR'HO$) groups and said y ($CH_2CR''HO$) groups may be arranged in any order; wherein x+y≤20 or even ≤10; wherein y≥1; and wherein independently each z=0 to 5;

(b) $(CH_2CH_2O)_x(CH_2C(OR)HCH_2O)_y(CH_2CH_2O)_{z'}H$, wherein each R is independently selected from the group consisting of H, $(CH_2CH_2O)^{z'}H$, and mixtures thereof; wherein groups indicated by indices x, y and z may be arranged in any order; wherein x+y≤5; wherein y≥1; and wherein independently z=0 to 10 and each z'=0 to 10;

(c) $CH_2CH(OR^6)CH_2OR^7$ wherein $R^6$ is selected from the group consisting of H, $(CH_2CH_2O)_zH$, and mixtures thereof; and wherein z=0 to 20; wherein $R^7$ is selected from the group consisting of $C_1$-$C_{16}$ alkyl, aryl groups, and mixtures thereof; and (d) the hydroxy addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 20 alkylene oxide units.

In a preferred whitening agent of the present invention, the index a is from about 0 to about 1; wherein $R^3$ is H; wherein $R^5$ is selected from the group consisting of:

(a) $(CH_2CR'HO)_x(CH_2CR''HO)_yH$ wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x ($CH_2CR'HO$) groups and said y ($CH_2CR''HO$) groups may be arranged in any order; wherein x+y≤20 or even ≤10; wherein y≥1; and wherein independently each z=0 to 5; and (b) $(CH_2CH_2O)_{x'}(CH_2C(OR)HCH_2O)_{y'}(CH_2CH_2O)^{z'}H$, wherein each R is independently selected from the group consisting of H, $(CH_2CH_2O)_{w'}H$, and mixtures thereof; wherein groups indicated by indices x', y' and z' may be arranged in any order; wherein x'+y'≤5; wherein y'≥1; wherein z'=0 to 10 and wherein independently each w'=0 to 10.

In another preferred whitening agent of the present invention, the index b=0; wherein $R^5$ is $(CH_2CR'HO)_x(CH_2CR''HO)_yH$; wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x ($CH_2CR'HO$) groups and said y ($CH_2CR''HO$) groups may be arranged in any order; wherein x+y≤20; wherein y≥1; and wherein independently each z=0 to 10.

As will be appreciated by those skilled in the art unreacted starting materials and additional components resulting from minor side reactions will typically be present at levels that are unlikely to significantly impact the whitening agent's performance, as perceived by the average consumer. As will further be appreciated, when present at levels that may impact the whitening agent's performance, or the overall performance of a detergent formulation containing the mixture, as perceived by the average consumer, such additional components may be removed or retained as desired.

The Test Methods provided below can be used to determine if a dye, or a mixture of dyes, is a whitening agent for the purposes of the present invention.

Test Methods

I. Method for Determining Deposition for a Dye a.) Unbrightened Multifiber Fabric Style 41 swatches (MFF41, 5 cm×10 cm, average weight 1.46 g) serged with unbrightened thread are purchased from Testfabrics, Inc. (West Pittston, Pa.). MFF41 swatches are stripped prior to use by washing two full cycles in AATCC heavy duty liquid laundry detergent (HDL) nil brightener at 49° C. and washing 3 additional full cycles at 49° C. without detergent. Four replicate swatches are placed into each flask.

b.) A sufficient volume of AATCC standard nil brightener HDL detergent solution is prepared by dissolving the detergent in 0 gpg water at room temperature at a concentration of 1.55 g per liter.

c.) A concentrated stock solution of dye is prepared in an appropriate solvent selected from dimethyl sulfoxide (DMSO), ethanol or 50:50 ethanol:water. Ethanol is preferred. The dye stock is added to a beaker containing 400 mL detergent solution (prepared in step I.b. above) in an amount sufficient to produce an aqueous solution absorbance at the $\lambda_{max}$ of 0.1 AU (±0.01 AU) in a cuvette of path length 1.0 cm. For a mixture of dyes, the sum of the aqueous solution absorbance at the $\lambda_{max}$ of the individual dyes is 0.1 AU (±0.01 AU) in a cuvette of path length 1.0 cm. Total organic solvent concentration in a wash solution from the concentrated stock solution is less than 0.5%. A 125 mL aliquot of the wash solution is placed into 3 separate disposable 250 mL Erlenmeyer flasks (Thermo Fisher Scientific, Rochester, N.Y.). Solution hardness is adjusted to 6 gpg by addition of an appropriate volume of 10,000 gpg Ca:Mg (3:1) hardness stock solution prepared in deionized water.

d.) Four MFF41 swatches are placed into each flask (which correlates to approximately a 25:1 liquor:fabric ratio), flasks are capped and manually shaken to wet the swatches. Flasks are placed onto a Model 75 wrist action shaker from Burrell Scientific, Inc. (Pittsburg, Pa.) and agitated on the highest setting of 10 (390 oscillations per minute with an arc of 14.6°). After 12 minutes, the wash solution is removed by vacuum aspiration, 125 mL of 0 gpg water is added for a rinse, hardness of the rinse water is adjusted to 6 gpg as noted above, and the flasks agitated for 4 additional minutes. Rinse solution is removed by vacuum aspiration and swatches are spun in a Mini Countertop Spin Dryer (The Laundry Alternative Inc., Nashua, N.H.) for 5 minutes, after which they are allowed to air dry in the dark.

e.) L*, a*, and b* values for the 2 most consumer relevant fabric types, cotton and polyester, are measured on the dry swatches using a LabScan XE reflectance spectrophotometer (HunterLabs, Reston, Va.; D65 illumination, 10° observer, UV light excluded). The L*, a*, and b* values of the 12 swatches (3 flasks each containing 4 swatches) are averaged and the hueing deposition (HD) of the dye is calculated for each fabric type using the following equation:

$$HD=DE^*=((L^*_c-L^*_s)^2+(a^*_c-a^*_s)^2+(b^*_c-b^*_s)^2)^{1/2}$$

wherein the subscripts c and s respectively refer to the control, i.e., the fabric washed in detergent with no dye, and the fabric washed in detergent containing dye, or a mixture of dyes, according to the method described above. The HD for any consumer relevant fabric, such as nylon, can be determined in the same manner.

II. Method for Determining Relative Hue Angle (vs. Nil Dye Control)

a) The a* and b* values of the 12 swatches from each solution were averaged and the following formulas used to determine Δa* and Δb*:

$$\Delta a^*=a^*_c-a^*_s \text{ and } \Delta b^*=b^*_c-b^*_s$$

wherein the subscripts c and s respectively refer to the fabric washed in detergent with no dye and the fabric washed in detergent containing dye, or mixture of dyes, according to the method described in I. above.

b.) If the absolute value of both Δa* and Δb*<0.25, no Relative Hue Angle (RHA) was calculated. If the absolute value of either Δa* or Δb* were ≥0.25, the RHA was determined using one of the following formulas:

$$\text{When } \Delta b^*\geq 0,\ RHA=A\ TAN\ 2(\Delta a^*,\Delta b^*)$$

$$\text{When } \Delta b^*<0,\ RHA=360+A\ TAN\ 2(\Delta a^*,\Delta b^*)$$

III. Method to Determine if a Dye is a Whitening Agent

A dye, or mixture of dyes, is considered a whitening agent (also known as a hueing dye) for the purposes of the present invention if (a) either the $HD_{cotton}$ or the $HD_{polyester}$ is greater than or equal to 2.0 DE* units or preferably greater than or equal to 3.0, or 4.0 or even 5.0, according to the formula above, and (b) the relative hue angle (see Method III. below) on the fabric that meets the DE* criterion in (a) is within 240 to 345, more preferably 260 to 325, even more preferably 270 to 310. If the value of HD for both fabric types is less than 2.0 DE* units, or if the relative hue angle is not within the prescribed range on each fabric for which the DE* meets the criteria the dye is not a shading dye for the purposes of the present invention.

The whitening agent's described in the present specification may be incorporated into a laundry care composition including but not limited to laundry detergents and fabric care compositions. Such compositions comprise one or more of said whitening agents and a laundry care ingredient. The whitening agent may be added to cellulose and other substrates using a variety of application techniques. For application to cellulose-containing and other textile substrates, the whitening agent is preferably included as an additive in laundry detergent. Thus, application to the textile substrate actually occurs when a consumer adds laundry detergent to a washing machine. Similarly, RAFS compositions are typically added in the rinse cycle, which is after the detergent solution has been used and replaced with the rinsing solution in typical laundering processes. For application to cellulosic paper substrates, the whitening agent may be added to the paper pulp mixture prior to formation of the final paper product.

The laundry care compositions including laundry detergents may be in solid or liquid form, including a gel form. The laundry care compositions including laundry detergents may also be in a unit dose pouch. The laundry detergent composition comprises a surfactant in an amount sufficient to provide desired cleaning properties.

The whitening agent may be present in the laundry detergent composition in an amount from about 0.0001% to about 10% by weight of the composition, more preferably from about 0.0001% to about 5% by weight of the composition, and even more preferably from about 0.0001% to about 1% by weight of the composition.

The laundry detergent composition comprises a surfactant in an amount sufficient to provide desired cleaning properties. In one embodiment, the laundry detergent composition comprises, by weight, from about 5% to about 90% of the surfactant, and more specifically from about 5% to about 70% of the surfactant, and even more specifically from about 5% to about 40%. The surfactant may comprise anionic, nonionic, cationic, zwitterionic and/or amphoteric surfactants. In a more specific embodiment, the detergent composition comprises anionic surfactant, nonionic surfactant, or mixtures thereof.

Suitable anionic surfactants useful herein can comprise any of the conventional anionic surfactant types typically used in liquid detergent products. These include the alkyl benzene sulfonic acids and their salts as well as alkoxylated or non-alkoxylated alkyl sulfate materials.

Exemplary anionic surfactants are the alkali metal salts of $C_{10-16}$ alkyl benzene sulfonic acids, preferably $C_{11-14}$ alkyl benzene sulfonic acids. Preferably the alkyl group is linear and such linear alkyl benzene sulfonates are known as "LAS". Alkyl benzene sulfonates, and particularly LAS, are well known in the art. Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$, e.g., $C_{12}$, LAS is a specific example of such surfactants.

Another exemplary type of anionic surfactant comprises ethoxylated alkyl sulfate surfactants. Such materials, also known as alkyl ether sulfates or alkyl polyethoxylate sulfates, are those which correspond to the formula: $R'—O—(C_2H_4O)_n—SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6 and M is sodium.

The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the compositions of this invention and used as or in any anionic surfactant component which may be present. Specific examples of non-alkoxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $ROSO_3^-M^+$ wherein R is typically a linear $C_8$-$C_{20}$ hydrocarbyl group, which may be straight chain or branched chain, and M is a water-solubilizing cation. In specific embodiments, R is a $C_{10}$-$C_{15}$ alkyl, and M is alkali metal, more specifically R is $C_{12}$-$C_{14}$ and M is sodium.

Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3) alkyl sulfates; d) $C_{10}$-$C_{18}$ alkyl alkoxy sulfates ($AE_xS$) wherein preferably x is from 1-30; e) $C_{10}$-$C_{18}$ alkyl alkoxy carboxylates preferably comprising 1-5 ethoxy units; f) mid-chain branched alkyl sulfates as discussed in U.S. Pat. No. 6,020,303 and U.S. Pat. No. 6,060,443; g) mid-chain branched alkyl alkoxy sulfates as discussed in U.S. Pat. No. 6,008,181 and U.S. Pat. No. 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

Suitable nonionic surfactants useful herein can comprise any of the conventional nonionic surfactant types typically used in liquid detergent products. These include alkoxylated fatty alcohols and amine oxide surfactants. Preferred for use in the liquid detergent products herein are those nonionic surfactants which are normally liquid.

Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_8$-$C_{16}$ alkyl group, m is from 2 to 4, and n ranges from about 2 to 12. Preferably $R^1$ is an alkyl group, which may be primary or secondary, that comprises from about 9 to 15 carbon atoms, more preferably from about 10 to 14 carbon atoms. In one embodiment, the alkoxylated fatty alcohols will also be ethoxylated materials that contain from about 2 to 12 ethylene oxide moieties per molecule, more preferably from about 3 to 10 or even from about 7 to 9 ethylene oxide moieties per molecule.

The alkoxylated fatty alcohol materials useful in the liquid detergent compositions herein will frequently have a hydrophilic-lipophilic balance (HLB) which ranges from about 3 to 17. More preferably, the HLB of this material will range from about 6 to 15, most preferably from about 8 to 15. Alkoxylated fatty alcohol nonionic surfactants have been marketed under the tradenames Neodol and Dobanol by the Shell Chemical Company.

Another suitable type of nonionic surfactant useful herein comprises the amine oxide surfactants. Amine oxides are materials which are often referred to in the art as "semi-polar" nonionics. Amine oxides have the formula: $R(EO)_x(PO)_y(BO)_zN(O)(CH_2R')_2.qH_2O$. In this formula, R is a relatively long-chain hydrocarbyl moiety which can be saturated or unsaturated, linear or branched, and can contain from 8 to 20, preferably from 10 to 16 carbon atoms, and is more preferably $C_{12}$-$C_{16}$ primary alkyl. R' is a short-chain moiety, preferably selected from hydrogen, methyl and $—CH_2OH$. When x+y+z is different from 0, EO is ethyleneoxy, PO is propyleneneoxy and BO is butyleneoxy. Amine oxide surfactants are illustrated by $C_{12-14}$ alkyldimethyl amine oxide.

Non-limiting examples of nonionic surfactants include: a) $C_{12}$-$C_{18}$ alkyl ethoxylates, such as, NEODOL® nonionic surfactants from Shell; b) $C_6$-$C_{12}$ alkyl phenol alkoxylates wherein the alkoxylate units are a mixture of ethyleneoxy and propyleneoxy units; c) $C_{12}$-$C_{18}$ alcohol and $C_6$-$C_{12}$ alkyl phenol condensates with ethylene oxide/propylene oxide block polymers such as Pluronic® from BASF; d) $C_{14}$-$C_{22}$ mid-chain branched alcohols, BA, as discussed in U.S. Pat. No. 6,150,322; e) $C_{14}$-$C_{22}$ mid-chain branched alkyl alkoxylates, $BAE_x$, wherein x if from 1-30, as discussed in U.S. Pat. No. 6,153,577, U.S. Pat. No. 6,020,303 and U.S. Pat. No. 6,093,856; f) Alkylpolysaccharides as discussed in U.S. Pat. No. 4,565,647 to Llenado, issued Jan. 26, 1986; specifically alkylpolyglycosides as discussed in U.S. Pat. No. 4,483,780 and U.S. Pat. No. 4,483,779; g) Polyhydroxy fatty acid amides as discussed in U.S. Pat. No. 5,332,528, WO 92/06162, WO 93/19146, WO 93/19038, and WO 94/09099; and h) ether capped poly(oxyalkylated) alcohol surfactants as discussed in U.S. Pat. No. 6,482,994 and WO 01/42408.

In the laundry detergent compositions herein, the detersive surfactant component may comprise combinations of anionic and nonionic surfactant materials. When this is the case, the weight ratio of anionic to nonionic will typically range from 10:90 to 90:10, more typically from 30:70 to 70:30. In general compositions with increasing weight ratios favoring nonionic surfactants may lead to increased deposition of the inventive whitening agents in a wash. Such factors must always be carefully weighed over against any risk elements that may also increase in these formulations. The ordinarily-skilled artisan is well aware of such factors and formulates accordingly.

Cationic surfactants are well known in the art and non-limiting examples of these include quaternary ammonium surfactants, which can have up to 26 carbon atoms. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002, WO 98/35003, WO 98/35004, WO 98/35005, and WO 98/35006; d) cationic ester surfactants as discussed in U.S. Pat. Nos. 4,228,042, 4,239,660 4,260,529 and U.S. Pat. No. 6,022,844; and e) amino surfactants as discussed in U.S. Pat. No. 6,221,825 and WO 00/47708, specifically amido propyldimethyl amine (APA).

Non-limiting examples of zwitterionic surfactants include derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants; betaine, including alkyl dimethyl betaine and cocodimethyl amidopropyl betaine, $C_8$ to $C_{18}$ (preferably $C_{12}$ to $C_{18}$) amine oxides and sulfo and hydroxy betaines, such as N-alkyl-N,N-dimethylammino-1-propane sulfonate where the alkyl group can be $C_8$ to $C_{18}$, preferably $C_{10}$ to $C_{14}$.

Non-limiting examples of ampholytic surfactants include aliphatic derivatives of secondary or tertiary amines, or aliphatic derivatives of heterocyclic secondary and tertiary amines in which the aliphatic radical can be straight- or branched-chain. One of the aliphatic substituents comprises at least about 8 carbon atoms, typically from about 8 to about 18 carbon atoms, and at least one comprises an anionic water-solubilizing group, e.g. carboxy, sulfonate, sulfate. See U.S. Pat. No. 3,929,678 to Laughlin et al., issued Dec. 30, 1975 at column 19, lines 18-35, for examples of ampholytic surfactants.

As noted, the compositions may be in the form of a solid, either in tablet or particulate form, including, but not limited to particles, flakes, or the like, or the compositions may be in the form of a liquid. The liquid detergent compositions comprise an aqueous, non-surface active liquid carrier. Generally, the amount of the aqueous, non-surface active liquid carrier employed in the compositions herein will be effective to solubilize, suspend or disperse the composition components. For example, the compositions may comprise, by weight, from about 5% to about 90%, more specifically from about 10% to about 70%, and even more specifically from about 20% to about 70% of the aqueous, non-surface active liquid carrier.

The most cost effective type of aqueous, non-surface active liquid carrier is, of course, water itself. Accordingly, the aqueous, non-surface active liquid carrier component will generally be mostly, if not completely, comprised of water. While other types of water-miscible liquids, such alkanols, diols, other polyols, ethers, amines, and the like, have been conventionally been added to liquid detergent compositions as co-solvents or stabilizers, for purposes of the present invention, the utilization of such water-miscible liquids should be minimized to hold down composition cost. Accordingly, the aqueous liquid carrier component of the liquid detergent products herein will generally comprise water present in concentrations ranging from about 5% to about 90%, more preferably from about 20% to about 70%, by weight of the composition.

Detergent compositions may also contain bleaching agents. Suitable bleaching agents include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A suitable percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

Compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

(a) Bleach Activators—

Preferably, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide, source leads to the in situ production of the peracid corresponding to the bleach activator. Various non-limiting examples of activators are disclosed in U.S. Pat. Nos. 5,576,282; 4,915,854 and 4,412, 934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 11 are those selected having an OBS or VL leaving group. Preferred hydrophobic bleach activators include, but are not limited to, nonanoyloxybenzenesulphonate (NOBS); 4-[N-(nonanoyl) amino hexanoyloxy]-benzene sulfonate sodium salt (NACA-OBS), an example of which is described in U.S. Pat. No. 5,523,434; dodecanoyloxybenzenesulphonate (LOBS or $C_{12}$-OBS); 10-undecenoyloxybenzenesulfonate (UDOBS or $C_{11}$-OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., and copending patent application Ser. No. 08/064,564, all of which are incorporated herein by reference.

The mole ratio of peroxygen source (as AvO) to bleach activator in the present invention generally ranges from at least 1:1, preferably from about 20:1, more preferably from about 10:1 to about 1:1, preferably to about 3:1.

Quaternary substituted bleach activators may also be included. The present laundry compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Highly preferred bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl) oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)═N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, are very useful herein, especially the acyl caprolactams (see for example WO 94-28102 A) and acyl valerolactams (see U.S. Pat. No. 5,503,639 to Willey et al. incorporated herein by reference).

(b) Organic Peroxides, Especially Diacyl Peroxides—

These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

(c) Metal-Containing Bleach Catalysts—

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

Manganese Metal Complexes—

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn^{IV}_2(u\text{-}O)_3$(1,4,7-trimethyl-1,4,7-triazacyclononane)$_2(PF_6)_2$, $Mn^{III}_2(u\text{-}O)_1(u\text{-}OAc)_2$(1,4,7-trimethyl-1,4,7-triazacyclononane)$_2(ClO_4)_2$, $Mn^{IV}_4(u\text{-}O)_6$(1,4,7-triazacyclononane)$_4(ClO_4)_4$, $Mn^{III}Mn^{IV}_4(u\text{-}O)_1(u\text{-}OAc)_2$-(1,4,7-trimethyl-1,4,7-triazacyclononane)$_2(ClO_4)_3$, $Mn^{IV}$(1,4,7-trimethyl-1,4,7-triazacyclononane)-$(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt Metal Complexes—

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorg. Bioinorg. Mech.*, (1983), 2, pages 1-94. The most preferred cobalt catalyst useful herein are cobalt pentaamine acetate salts having the formula $[Co(NH_3)_5OAc]\ T_y$, wherein "OAc" represents an acetate moiety and "$T_y$" is an anion, and especially cobalt pentaamine acetate chloride, $[Co(NH_3)_5OAc]Cl_2$; as well as $[CO(NH_3)_5OAc](OAc)_2$; $[CO(NH_3)_5OAc](PF_6)_2$; $[CO(NH_3)_5OAc](SO_4)$; $[CO—(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 6,302,921; 6,287,580; 6,140,294; 5,597,936; 5,595,967; and 5,703,030; in the Tobe article and the references cited therein; and in U.S. Pat. No. 4,810,410; *J. Chem. Ed.* (1989), 66 (12), 1043-45; The Synthesis and Characterization of Inorganic Compounds, W. L. Jolly (Prentice-Hall; 1970), pp. 461-3; *Inorg. Chem.,* 18, 1497-1502 (1979); *Inorg. Chem.,* 21, 2881-2885 (1982); *Inorg. Chem.,* 18, 2023-2025 (1979); Inorg. Synthesis, 173-176 (1960); and *Journal of Physical Chemistry,* 56, 22-25 (1952).

Transition Metal Complexes of Macropolycyclic Rigid Ligands—

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or laundry uses, and are non-limitingly illustrated by any of the following:

Dichloro-5,12-dimethyl-1,5,8,12-tetraazabicyclo[6.6.2] hexadecane Manganese(II)

Dichloro-5,12-diethyl-1,5,8,12-tetraazabicyclo[6.6.2]hexadecane Manganese(II)

Diaquo-5,12-dimethyl-1,5,8,12-tetraazabicyclo[6.6.2]hexadecaneManganese(II) Hexafluorophosphate Diaquo-5,12-diethyl-1,5,8,12-tetraazabicyclo[6.6.2]hexadecaneManganese(II) Hexafluorophosphate Aquo-hydroxy-5,12-dimethyl-1,5,8,12-tetraazabicyclo [6.6.2]hexadecane Manganese(III) Hexafluorophosphate Diaquo-5,12-dimethyl-1,5,8,12-tetraazabicyclo[6.6.2]hexadecaneManganese(II) Tetrafluoroborate Dichloro-5,12-dimethyl-1,5,8,12 tetraazabicyclo[6.6.2] hexadecane Manganese(III) Hexafluorophosphate Dichloro-5,12-diethyl-1,5,8,12-tetraazabicyclo[6.6.2]hexadecaneManganese(III) Hexafluorophosphate Dichloro-5,12-di-n-butyl-1,5,8,12-tetraaza bicyclo[6.6.2] hexadecane Manganese(II)

Dichloro-5,12-dibenzyl-1,5,8,12-tetraazabicyclo[6.6.2] hexadecaneManganese(II)

Dichloro-5-n-butyl-12-methyl-1,5,8,12-tetraaza-bicyclo [6.6.2]hexadecane Manganese(II)

Dichloro-5-n-octyl-12-methyl-1,5,8,12-tetraaza-bicyclo [6.6.2]hexadecane Manganese(II)

Dichloro-5-n-butyl-12-methyl-1,5,8,12-tetraaza-bicyclo [6.6.2]hexadecane Manganese(II).

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

(d) Bleach Boosting Compounds—

The compositions herein may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

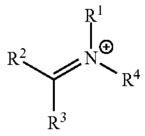

[I]

where $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source employed in the present invention may comprise any of these well known sources, including peroxygen compounds as well as compounds, which under consumer use conditions, provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. The bleach boosting compounds, when present, are preferably employed in conjunction with a peroxygen source in the bleaching systems of the present invention.

(e) Preformed Peracids—

Also suitable as bleaching agents are preformed peracids. The preformed peracid compound as used herein is any convenient compound which is stable and which under consumer use conditions provides an effective amount of peracid or peracid anion. The preformed peracid compound may be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

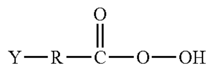

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

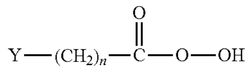

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

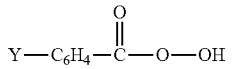

wherein Y can be, for example, hydrogen, alkyl, alkylhalogen, halogen, C(O)OH or C(O)OOH.

Typical monoperoxy acids useful herein include alkyl and aryl peroxyacids such as:

(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);

(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);

(iii) amidoperoxyacids, e.g. monononylamide of either peroxysuccinic acid (NAPSA) or of peroxyadipic acid (NAPAA).

Typical diperoxyacids useful herein include alkyl diperoxyacids and aryldiperoxyacids, such as:

(i) 1,12-diperoxydodecanedioic acid;

(ii) 1,9-diperoxyazelaic acid;

(iii) diperoxybrassylic acid; diperoxysebacic acid and diperoxyisophthalic acid;

(iv) 2-decyldiperoxybutane-1,4-dioic acid;

(v) 4,4'-sulfonylbisperoxybenzoic acid.

Such bleaching agents are disclosed in U.S. Pat. No. 4,483,781 to Hartman and U.S. Pat. No. 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, Del. can also be employed as a suitable source of peroxymonosulfuric acid. PAP is disclosed in, for example, U.S. Pat. Nos. 5,487,818; 5,310,934; 5,246,620; 5,279,757 and 5,132,431.

(f) Photobleaches—

Suitable photobleaches for use in the treating compositions of the present invention include, but are not limited to, the photobleaches described in U.S. Pat. Nos. 4,217,105 and 5,916,481.

(g) Enzyme Bleaching—

Enzymatic systems may be used as bleaching agents. The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

The present invention compositions and methods may utilize alternative bleach systems such as ozone, chlorine dioxide and the like. Bleaching with ozone may be accomplished by introducing ozone-containing gas having ozone content from about 20 to about 300 $g/m^3$ into the solution that is to contact the fabrics. The gas:liquid ratio in the solution should be maintained from about 1:2.5 to about 1:6. U.S. Pat. No. 5,346,588 describes a process for the utilization of ozone as an alternative to conventional bleach systems and is herein incorporated by reference.

The detergent compositions of the present invention may also include any number of additional optional ingredients. These include conventional laundry detergent composition components such as non-tinting dyes, detersive builders, enzymes, enzyme stabilizers (such as propylene glycol, boric acid and/or borax), suds suppressors, soil suspending agents, soil release agents, other fabric care benefit agents, pH adjusting agents, chelating agents, smectite clays, solvents, hydrotropes and phase stabilizers, structuring agents, dye transfer inhibiting agents, opacifying agents, optical brighteners, perfumes and coloring agents. The various optional detergent composition ingredients, if present in the compositions herein, should be utilized at concentrations conventionally employed to bring about their desired contribution to the composition or the laundering operation. Frequently, the total amount of such optional detergent composition ingredients can range from about 0.01% to about 50%, more preferably from about 0.1% to about 30%, by weight of the composition.

The liquid detergent compositions are in the form of an aqueous solution or uniform dispersion or suspension of surfactant, whitening agent, and certain optional other ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable and will typically have a viscosity which ranges from about 100 to 600 cps, more preferably from about 150 to 400 cps. For purposes of this invention, viscosity is measured with a Brookfield LVDV-II+ viscometer apparatus using a #21 spindle.

The liquid detergent compositions herein can be prepared by combining the components thereof in any convenient order and by mixing, e.g., agitating, the resulting component combination to form a phase stable liquid detergent composition. In a preferred process for preparing such compositions, a liquid matrix is formed containing at least a major proportion, and preferably substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In an alternate embodiment for forming the liquid detergent compositions, the whitening agent is first combined with one or more liquid components to form a whitening agent premix, and this whitening agent premix is added to a composition formulation containing a substantial portion, for example more than 50% by weight, more specifically, more than 70% by weight, and yet more specifically, more than 90% by weight, of the balance of components of the laundry detergent composition. For example, in the methodology described above, both the whitening agent premix and the enzyme component are added at a final stage of component additions. In a further embodiment, the whitening agent is encapsulated prior to addition to the detergent composition, the encapsulated whitening agent is suspended in a structured liquid, and the suspension is added to a composition formulation containing a substantial portion of the balance of components of the laundry detergent composition.

As noted previously, the detergent compositions may be in a solid form. Suitable solid forms include tablets and particulate forms, for example, granular particles or flakes. Various techniques for forming detergent compositions in such solid forms are well known in the art and may be used herein. In one embodiment, for example when the composition is in the form of a granular particle, the whitening agent is provided in particulate form, optionally including additional but not all components of the laundry detergent composition. The whitening agent particulate is combined with one or more additional particulates containing a balance of components of the laundry detergent composition. Further, the whitening agent, optionally including additional but not all components of the laundry detergent composition, may be provided in an encapsulated form, and the whitening agent encapsulate is combined with particulates containing a substantial balance of components of the laundry detergent composition.

The compositions of this invention, prepared as hereinbefore described, can be used to form aqueous washing solutions for use in the laundering of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the liquid detergent compositions herein added to water to form aqueous laundering solutions can comprise amounts sufficient to form from about 500 to 7,000 ppm of composition in aqueous washing solution. More preferably, from about 1,000 to 3,000 ppm of the detergent compositions herein will be provided in aqueous washing solution.

Fabric Care Compositions/Rinse Added Fabric Softening Compositions

In another specific embodiment, the whitening agents of the present invention may be included in a fabric care composition. The fabric care composition may be comprised of at least one whitening agent and a rinse added fabric softening composition ("RAFS;" also known as rinse added fabric conditioning compositions). Examples of typical rinse added softening compositions can be found in U.S. Provisional Patent Application Ser. No. 60/687582 filed on Oct. 8, 2004. The rinse added fabric softening compositions of the present invention may comprise (a) fabric softening active and (b) a thiazolium dye. The rinse added fabric softening composition may comprise from about 1% to about 90% by weight of the FSA, more preferably from about 5% to about 50% by weight of the FSA. The whitening agent may be present in the rinse added fabric softening composition in an amount from about 0.5 ppb to about 50 ppm, more preferably from about 0.5 ppm to about 30 ppm.

In one embodiment of the invention, the fabric softening active (hereinafter "FSA") is a quaternary ammonium compound suitable for softening fabric in a rinse step. In one embodiment, the FSA is formed from a reaction product of a fatty acid and an aminoalcohol obtaining mixtures of mono-, di-, and, in one embodiment, triester compounds. In another embodiment, the FSA comprises one or more softener quaternary ammonium compounds such, but not limited to, as a monoalkyquaternary ammonium compound, a diamido quaternary compound and a diester quaternary ammonium compound, or a combination thereof.

In one aspect of the invention, the FSA comprises a diester quaternary ammonium (hereinafter "DQA") compound composition. In certain embodiments of the present invention, the DQA compounds compositions also encompasses a description of diamido FSAs and FSAs with mixed amido and ester linkages as well as the aforementioned diester linkages, all herein referred to as DQA.

A first type of DQA ("DQA (1)") suitable as a FSA in the present CFSC includes a compound comprising the formula:

$$\{R_{4-m}—N^+—[(CH_2)_n—Y—R^1]_m\}X^-$$

wherein each R substituent is either hydrogen, a short chain $C_1$-$C_6$, preferably $C_1$-$C_3$ alkyl or hydroxyalkyl group, e.g., methyl (most preferred), ethyl, propyl, hydroxyethyl, and the like, poly ($C_{2-3}$ alkoxy), preferably polyethoxy, group, benzyl, or mixtures thereof; each m is 2 or 3; each n is from 1 to about 4, preferably 2; each Y is —O—(O)C—, —C(O)—O—, —NR—C(O)—, or —C(O)—NR— and it is acceptable for each Y to be the same or different; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group; it is acceptable for $R^1$ to be unsaturated or saturated and branched or linear and preferably it is linear; it is acceptable for each $R^1$ to be the same or different and preferably these are the same; and $X^-$ can be any softener-compatible anion, preferably, chloride, bromide, methylsulfate, ethylsulfate, sulfate, phosphate, and nitrate, more preferably chloride or methyl sulfate. Preferred DQA compounds are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyl-oxyethyl)-N,N-methylhydroxyethylammonium methylsulfate wherein the acyl group is derived from animal fats, unsaturated, and polyunsaturated, fatty acids, e.g., tallow, hardended tallow, oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, palm oil, etc.

Non-limiting examples of suitable fatty acids are listed in U.S. Pat. No. 5,759,990 at column 4, lines 45-66. In one embodiment, the FSA comprises other actives in addition to DQA (1) or DQA. In yet another embodiment, the FSA comprises only DQA (1) or DQA and is free or essentially free of any other quaternary ammonium compounds or other actives. In yet another embodiment, the FSA comprises the precursor amine that is used to produce the DQA.

In another aspect of the invention, the FSA comprises a compound, identified as DTTMAC comprising the formula:

$$[R_{4-m}—N^{(+)}—R^1_m]A^-$$

wherein each m is 2 or 3, each $R^1$ is a $C_6$-$C_{22}$, preferably $C_{14}$-$C_{20}$, but no more than one being less than about $C_{12}$ and then the other is at least about 16, hydrocarbyl, or substituted hydrocarbyl substituent, preferably $C_{10}$-$C_{20}$ alkyl or alkenyl (unsaturated alkyl, including polyunsaturated alkyl, also referred to sometimes as "alkylene"), most preferably $C_{12}$-$C_{18}$ alkyl or alkenyl, and branch or unbranched. In one embodiment, the Iodine Value (IV) of the FSA is from about 1 to 70; each R is H or a short chain $C_1$-$C_6$, preferably $C_1$-$C_3$ alkyl or hydroxyalkyl group, e.g., methyl (most preferred), ethyl, propyl, hydroxyethyl, and the like, benzyl, or $(R^2O)_{2-4}H$ where each $R^2$ is a $C_{1-6}$ alkylene group; and $A^-$ is a softener compatible anion, preferably, chloride, bromide, methylsulfate, ethylsulfate, sulfate, phosphate, or nitrate; more preferably chloride or methyl sulfate.

Examples of these FSAs include dialkydimethylammonium salts and dialkylenedimethylammonium salts such as ditallowdimethylammonium and ditallowdimethylammonium methylsulfate. Examples of commercially available dialkylenedimethylammonium salts usable in the present invention are di-hydrogenated tallow dimethyl ammonium chloride and ditallowdimethyl ammonium chloride available from Degussa under the trade names Adogen® 442 and Adogen® 470 respectively. In one embodiment, the FSA comprises other actives in addition to DTTMAC. In yet another embodiment, the FSA comprises only compounds of the DTTMAC and is free or essentially free of any other quaternary ammonium compounds or other actives.

In one embodiment, the FSA comprises an FSA described in U.S. Pat. Pub. No. 2004/0204337 A1, published Oct. 14, 2004 to Corona et al., from paragraphs 30-79. In another embodiment, the FSA is one described in U.S. Pat. Pub. No. 2004/0229769 A1, published Nov. 18, 2005, to Smith et al., on paragraphs 26-31; or U.S. Pat. No. 6,494,920, at column 1, line 51 et seq. detailing an "esterquat" or a quaternized fatty acid triethanolamine ester salt.

In one embodiment, the FSA is chosen from at least one of the following: ditallowoyloxyethyl dimethyl ammonium chloride, dihydrogenated-tallowoyloxyethyl dimethyl ammonium chloride, ditallow dimethyl ammonium chloride, ditallowoyloxyethyl dimethyl ammonium methyl sulfate, dihydrogenated-tallowoyloxyethyl dimethyl ammonium chloride, dihydrogenated-tallowoyloxyethyl dimethyl ammonium chloride, or combinations thereof.

In one embodiment, the FSA may also include amide containing compound compositions. Examples of diamide comprising compounds may include but not limited to methyl-bis(tallowamidoethyl)-2-hydroxyethylammonium methyl sulfate (available from Degussa under the trade names Varisoft 110 and Varisoft 222). An example of an amide-ester containing compound is N-[3-(stearoylamino)propyl]-N-[2-(stearoyloxy)ethoxy)ethyl)]-N-methylamine. Another specific embodiment of the invention provides for a rinse added fabric softening composition further comprising a cationic starch. Cationic starches are disclosed in US 2004/0204337 A1. In one embodiment, the rinse added fabric softening composition comprises from about 0.1% to about 7% of cationic starch by weight of the fabric softening composition. In one embodiment, the cationic starch is HCP401 from National Starch.

Suitable Laundry Care Ingredients

While not essential for the purposes of the present invention, the non-limiting list of laundry care ingredients illustrated hereinafter are suitable for use in the laundry care compositions and may be desirably incorporated in certain embodiments of the invention, for example to assist or enhance performance, for treatment of the substrate to be cleaned, or to modify the aesthetics of the composition as is the case with perfumes, colorants, dyes or the like. For example, to obtain other aesthetic colors in a detergent, the present dyes may be mixed with additional dyes or colorants, such as with a blue triphenylmethane dye. It is understood that such ingredients are in addition to the components that were previously listed for any particular embodiment. The total amount of such adjuncts may range from about 0.1% to about 50%, or even from about 1% to about 30%, by weight of the laundry care composition.

The precise nature of these additional components, and levels of incorporation thereof, will depend on the physical form of the composition and the nature of the operation for which it is to be used. Suitable laundry care ingredients include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the laundry care ingredients are not essential to Applicants' laundry care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Exemplary Detergent Formulations

Table 1 provides examples of liquid detergent formulations which include at least one whitening agent of the present invention.

TABLE 1

Liquid Detergent Formulations Comprising the Present Whitening Agent

| Ingredient | 1a wt % | 1b wt % | 1c wt % | 1d wt % | 1e wt % | 1f[4] wt % |
|---|---|---|---|---|---|---|
| sodium alkyl ether sulfate | 14.4% | 14.4% | | 9.2% | 5.4% | |
| linear alkylbenzene sulfonic acid | 4.4% | 4.4% | 12.2% | 5.7% | 1.3% | 22.0% |

TABLE 1-continued

Liquid Detergent Formulations Comprising the Present Whitening Agent

| Ingredient | 1a wt % | 1b wt % | 1c wt % | 1d wt % | 1e wt % | 1f[4] wt % |
|---|---|---|---|---|---|---|
| alkyl ethoxylate | 2.2% | 2.2% | 8.8% | 8.1% | 3.4% | 18.0% |
| amine oxide | 0.7% | 0.7% | 1.5% | | | |
| citric acid | 2.0% | 2.0% | 3.4% | 1.9% | 1.0% | 1.6% |
| fatty acid | 3.0% | 3.0% | 8.3% | | | 16.0% |
| protease | 1.0% | 1.0% | 0.7% | 1.0% | | 2.5% |
| amylase | 0.2% | 0.2% | 0.2% | | | 0.3% |
| lipase | | | | 0.2% | | |
| borax | 1.5% | 1.5% | 2.4% | 2.9% | | |
| calcium and sodium formate | 0.2% | 0.2% | | | | |
| formic acid | | | | | | 1.1% |
| amine ethoxylate polymers | 1.8% | 1.8% | 2.1% | | | 3.2% |
| sodium polyacrylate | | | | | 0.2% | |
| sodium polyacrylate copolymer | | | | 0.6% | | |
| DTPA[1] | 0.1% | 0.1% | | | | 0.9% |
| DTPMP[2] | | | 0.3% | | | |
| EDTA[3] | | | | | 0.1% | |
| fluorescent whitening agent | 0.15% | 0.15% | 0.2% | 0.12% | 0.12% | 0.2% |
| ethanol | 2.5% | 2.5% | 1.4% | 1.5% | | |
| propanediol | 6.6% | 6.6% | 4.9% | 4.0% | | 15.7% |
| sorbitol | | | | 4.0% | | |
| ethanolamine | 1.5% | 1.5% | 0.8% | 0.1% | | 11.0% |
| sodium hydroxide | 3.0% | 3.0% | 4.9% | 1.9% | 1.0% | |
| sodium cumene sulfonate | | | 2.0% | | | |
| silicone suds suppressor | | | 0.01% | | | |
| perfume | 0.3% | 0.3% | 0.7% | 0.3% | 0.4% | 0.6% |
| Whitening Agent | 0.013% | 0.001% | 0.005% | 0.003% | 0.0005% | 0.001% |
| water | balance | balance | balance | balance | balance | balance |
| | 100.0% | 100.0% | 100.0% | 100.0% | 100.0% | 100.0% |

[1]diethylenetriaminepentaacetic acid, sodium salt
[2]diethylenetriaminepentakismethylenephosphonic acid, sodium salt
[3]ethylenediaminetetraacetic acid, sodium salt
[4]a compact formula, packaged as a unitized dose in polyvinyl alcohol film

Granular Detergent Formulations

Table 2 provides examples of granular detergent formulations which include at least one whitening agent of the present invention.

TABLE 2

Granular Detergent Formulations Comprising the Present Whitening Agent

| Ingredient | 2a wt % | 2b wt % | 2c wt % | 2d wt % | 2e wt % |
|---|---|---|---|---|---|
| Na linear alkylbenzene sulfonate | 3.4% | 3.3% | 11.0% | 3.4% | 3.3% |
| Na alkylsulfate | 4.0% | 4.1% | | 4.0% | 4.1% |
| Na alkyl sulfate (branched) | 9.4% | 9.6% | | 9.4% | 9.6% |
| alkyl ethoxylate | | | 3.5% | | |
| type A zeolite | 37.4% | 35.4% | 26.8% | 37.4% | 35.4% |
| sodium carbonate | 22.3% | 22.5% | 35.9% | 22.3% | 22.5% |
| sodium sulfate | 1.0% | | 18.8% | 1.0% | |
| sodium silicate | | | 2.2% | | |
| protease | 0.1% | 0.2% | | 0.1% | 0.2% |
| sodium polyacrylate | 1.0% | 1.2% | 0.7% | 1.0% | 1.2% |
| carboxymethylcellulose | | | 0.1% | | |
| PEG 600 | | 0.5% | | | 0.5% |
| PEG 4000 | | 2.2% | | | 2.2% |
| DTPA | 0.7% | 0.6% | | 0.7% | 0.6% |
| fluorescent whitening agent | 0.1% | 0.1% | 0.1% | 0.1% | 0.1% |
| sodium percarbonate | | 5.0% | | | 5.0% |
| sodium nonanoyloxybenzenesulfonate | | 5.3% | | | 5.3% |
| silicone suds suppressor | 0.02% | 0.02% | | 0.02% | 0.02% |
| perfume | 0.3% | 0.3% | 0.2% | 0.3% | 0.3% |
| Whitening Agent | 0.004% | 0.006% | 0.002% | 0.004% | 0.02% |
| water and miscellaneous | balance | balance | balance | balance | balance |
| | 100.0% | 100.0% | 100.0% | 100.0% | 100.0% |

Exemplary Fabric Care Compositions

Table 3 provides examples of liquid fabric care compositions which include at least one whitening agent of the present invention.

TABLE 3

| Liquid Fabric Care Compositions Comprising the Present Whitening Agent | | | | |
|---|---|---|---|---|
| Ingredients | 3a | 3b | 3c | 3d |
| Fabric Softening Active [a] | 13.70% | 13.70% | 13.70% | 13.70% |
| Ethanol | 2.14% | 2.14% | 2.14% | 2.14% |
| Cationic Starch [b] | 2.17% | 2.17% | 2.17% | 2.17% |
| Perfume | 1.45% | 1.45% | 1.45% | 1.45% |
| Phase Stabilizing Polymer [c] | 0.21% | 0.21% | 0.21% | 0.21% |
| Calcium Chloride | 0.147% | 0.147% | 0.147% | 0.147% |
| DTPA [d] | 0.007% | 0.007% | 0.007% | 0.007% |
| Preservative [e] | 5 ppm | 5 ppm | 5 ppm | 5 ppm |
| Antifoam [f] | 0.015% | 0.015% | 0.015% | 0.015% |
| Whitening Agent | 30 ppm | 30 ppm | 30 ppm | 15 ppm |
| Tinopal CBS-X [g] | 0.2 | 0.2 | 0.2 | 0.2 |
| Ethoquad C/25 [h] | 0.26 | 0.26 | 0.26 | 0.26 |
| Ammonium Chloride | 0.1% | 0.1% | 0.1% | 0.1% |
| Hydrochloric Acid | 0.012% | 0.012% | 0.012% | 0.012% |
| Deionized Water | Balance | Balance | Balance | Balance |

[a] N,N-di(tallowoyloxyethyl)-N,N-dimethylammonium chloride.

[b] Cationic starch based on common maize starch or potato starch, containing 25% to 95% amylose and a degree of substitution of from 0.02 to 0.09, and having a viscosity measured as Water Fluidity having a value from 50 to 84.

[c] Copolymer of ethylene oxide and terephthalate having the formula described in U.S. Pat. No. 5,574,179 at col. 15, lines 1-5, wherein each X is methyl, each n is 40, u is 4, each $R^1$ is essentially 1,4-phenylene moieties, each $R^2$ is essentially ethylene, 1,2-propylene moieties, or mixtures thereof.

[d] Diethylenetriaminepentaacetic acid.

[e] KATHON ® CG available from Rohm and Haas Co.

[f] Silicone antifoam agent available from Dow Corning Corp. under the trade name DC2310.

[g] Disodium 4,4'-bis-(2-sulfostyryl) biphenyl, available from Ciba Specialty Chemicals.

[h] Cocomethyl ethoxylated [15] ammonium chloride, available from Akzo Nobel.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laundry care composition comprising a laundry care ingredient and a whitening agent, wherein the whitening agent is a nonionic amphiphilic polymeric oxygen-linked dye having the structure of Formula I:

Formula I

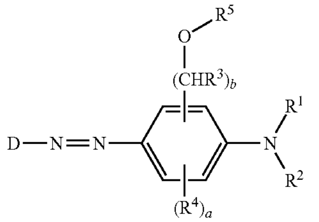

wherein each $R^4$ is independently selected from the group consisting of alkyl, oxyalkyl, oxyaryl, sulfonamidoalkyl, sulfonamidoaryl, amidoalkyl, amidodialkyl, amidoaryl, amidodiaryl, halogen, thioalkyl and thioaryl;

wherein the index a is an integer from about 0 to about 3; the index b is an integer from about 0 to about 1;

wherein D is an aromatic or heteroaromatic group;

wherein $R^1$ and $R^2$ are independently selected from the group consisting of H and $C_1$ to $C_{12}$ alkyl chains;

wherein $R^3$ is selected from H and $C_1$-$C_6$ alkyl;

wherein $R^5$ is selected from the group consisting of:

(a) $[(CH_2CR'HO)_x(CH_2CR''HO)_xH]$ wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x ($CH_2CR'HO$) groups and said y ($CH_2CR''HO$) groups may be arranged in any order; wherein x+y≤10; wherein y≥1; and wherein independently each z=0 to 5;

(b) $(CH_2CH_2O)_x(CH_2C(OR)HCH_2O)_y(CH_2CH_2O)_zH$, wherein each R is independently selected from the group consisting of H, $(CH_2CH_2O)_{z'}$, H and mixtures thereof; wherein groups indicated by indices x, y and z may be arranged in any order; wherein x+y≤5; wherein y≥1; and wherein independently z=0 to 10 and each z'=0 to 10;

(c) $CH_2CH(OR^6)CH_2OR^7$ wherein $R^6$ is selected from the group consisting of H, $(CH_2CH_2O)_zH$, and mixtures thereof; and wherein z=0 to 20; wherein $R^7$ is selected from the group consisting of $C_1$-$C_{16}$ alkyl, aryl groups, and mixtures thereof; and (d) the hydroxy addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 20 alkylene oxide units.

2. A laundry care composition according to claim 1, wherein the index a is from about 0 to about 1; wherein $R^3$ is H; wherein $R^5$ is selected from the group consisting of:

(a) $(CH_2CR'HO)_x(CH_2CR''\ HO)_yH$ wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x ($CH_2CR'HO$) groups and said y ($CH_2CR''HO$) groups may be arranged in any order; wherein x+y≤20; wherein y≥1; and wherein independently each z=0 to 5; and (b) $(CH_2CH_2O)_{x'}(CH_2C(OR)HCH_2O)_{y'}(CH_2CH_2O)_{z'}H$, wherein each R is independently selected from the group consisting of H, $(CH_2CH_2O)_{w'}H$, and mixtures thereof; wherein groups indicated by indices x', y' and z' may be arranged in any order; wherein x'+y'≤5; wherein y'≥1; wherein z'=0 to 10 and wherein independently each w'=0 to 10.

3. A laundry care composition according to claim 2, wherein the index b=0; wherein $R^5$ is $(CH_2CR'HO)_x(CH_2CR''HO)_yH$; wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein said x $(CH_2CR'HO)$ groups and said y $(CH_2CR''HO)$ groups may be arranged in any order; wherein x+y≤20; wherein y≥1; and wherein independently each z=0 to 10.

4. A laundry care composition according to claim 3, wherein R' and R" are H.

5. A laundry care composition according to claim 1, wherein the composition comprises a first wash lipase.

6. A laundry care composition according to claim 1, wherein the composition comprises a fluorescent agent selected from the group consisting of sodium 2 (4-styryl-3-sulfophenyl)-2H-napthol [1,2-djtriazole, disodium 4,4'-bis{[(4-anilino-6-{N methyl-N-2 hydroxyethyl) amino 1,3,5-triazin-2-yl)]amino}stilbeno-2-2' disulfonate, disodium 4,4'-bis [(4-anilino-6-morpholino-1,3,5-triazin-2-yl) amino] stilbene-2-2' disulfonate, and disodium 4,4'-bis (2-sulfostyryl) biphenyl, and mixtures thereof.

7. A laundry care composition according to claim 1, wherein the composition comprises a dye transfer inhibitor selected from the group consisting of:

(a) polyvinylpyrrolidone polymers;
(b) polyamine N-oxide polymers;
(c) copolymers of N-vinylpyrrolidone and N-vinylimidazole;
(d) polyvinyloxazolidones;
(e) polyvinylimidazoles; and
(f) mixtures thereof.

8. A laundry care composition according to claim 1, wherein the laundry care composition is a unit dose pouch.

9. A laundry care composition according to claim 1, wherein the composition comprises a total of no more than about 20 wt % water.

10. A laundry care composition according to claim 1, wherein the composition comprises a perfume microcapsule having a D[4,3] average particle of from about 0.01 microns to about 200 micrometers.

11. A method of treating a cellulosic and/or polyester and/or nylon-comprising textile, the method comprising the steps of:

(i) treating the textile with an aqueous solution comprising a laundry care composition according to claim 1, wherein the concentration of amphiphilic polymeric oxygen-linked nonionic dye is from about 1 ppb to about 500 ppm;
(ii) optionally rinsing, and
(iii) drying the textile.

* * * * *